United States Patent [19]

Wolfbeis et al.

[11] Patent Number: 4,892,640
[45] Date of Patent: Jan. 9, 1990

[54] SENSOR FOR THE DETERMINATION OF ELECTROLYTE CONCENTRATIONS

[75] Inventors: Otto S. Wolfbeis, Graz, Austria; Petra Braun geb. Hochmuth, Munzbach, Luxembourg

[73] Assignee: AVL AG, Switzerland

[21] Appl. No.: 218,445

[22] Filed: Jul. 12, 1988

[30] Foreign Application Priority Data

Apr. 16, 1985 [AT] Austria ................... 1148/85

[51] Int. Cl.$^4$ ........................................... G01N 27/46
[52] U.S. Cl. ..................... 204/418; 204/1 T; 204/403; 204/416; 250/458.1; 250/459.1; 356/317
[58] Field of Search ............... 204/1 T, 403, 416-420; 250/458.1, 459.1; 324/96; 356/317, 318

[56] References Cited

U.S. PATENT DOCUMENTS

| | | | |
|---|---|---|---|
| 3,932,233 | 1/1976 | Ruzicka et al. | 204/418 |
| 4,115,209 | 9/1978 | Freiser et al. | 204/418 |
| 4,306,877 | 12/1981 | Lubbers | 204/415 |
| 4,476,005 | 10/1984 | Tokinaga et al. | 204/403 |
| 4,502,937 | 3/1985 | Yagi | 204/416 |
| 4,547,729 | 10/1985 | Adolfsson et al. | 324/96 |
| 4,560,881 | 12/1985 | Briggs | 250/458.1 |
| 4,582,809 | 4/1986 | Block | 250/458.1 |
| 4,591,550 | 5/1986 | Hafeman et al. | 204/403 |

FOREIGN PATENT DOCUMENTS

81/02218 8/1981 PCT Int'l Appl. .

OTHER PUBLICATIONS

Munkholm et al., *Anal. Chem.*, 1986, 58, 1427.
Fuh et al., *Analyst*, 1987, 112, 1159.
Wolfbeis et al., "Optical Sensors: An Ion-Selective Optrode for Potassium" in Analytica Chimica Acta, 198 (1987), 1-12.
Schaffer et al., "Optical Sensors-Part 23-Effect of Langmuir-Blodgett Layer Composition on the Response of Ion-Selective Optrodes for Potassium, Based on the Fluorimetric Measurement of Membrane Potential" in Analyst, 113 (May 1988), 693-697.

*Primary Examiner*—T. Tung
*Attorney, Agent, or Firm*—Watson, Cole, Grindle & Watson

[57] ABSTRACT

An ion-selective electrode for determining an electrolyte concentration in an aqueous solution includes an ion-selective layer and a potential-sensitive fluorescent indicator in the ion-selective layer, the fluorescence intensity of the potential-sensitive fluorescent indicator being measured to provide an indication of the electrolyte concentration.

14 Claims, 2 Drawing Sheets

SENSOR FOR THE DETERMINATION OF ELECTROLYTE CONCENTRATIONS

This application is a continuation of application Ser. No. 851,582, filed Apr. 14, 1986, now abandoned.

BACKGROUND OF THE INVENTION

The present invention relates to a sensor for determining the concentration of an electrolyte in an aqueous solution using an ion-selective membrane which may be brought into contact with the sample solution, the potential difference arising at the electrode surface corresponding to the concentration of the electrolyte.

DESCRIPTION OF THE PRIOR ART

Sensors of this kind are known as ion-selective electrodes (ISEs). The electrodes are coated with a material which is permeable for a specific electrolyte only. This selective permeability, i.e., for one special electrolyte only, is achieved by the addition of so-called carrier molecules. Carrier molecules are molecules which are suitable for bonding certain ions in a specific manner, thus enhancing their diffusion from an aqueous phase into a hydrophobic one. The resulting potential difference at the electrode surface is measured electrochemically, such that the electrolyte concentration may be directly inferred, given suitable calibration.

An ion-selective electrode of the above type is described, for instance, in WO 81/02218-A1, FIG. 3, with an ion-selective outer layer that is permeable for potassium ions only. An example of a very specific ion carrier is valinomycin, which is able to carry the potassium ions into lipid membranes very specifically, even in the presence of a large surplus of sodium ions.

Ion-selective electrodes are the foundation of many new methods for determining the concentrations of electrolytes in aqueous solutions, above all in blood (i.e., mainly lithium, sodium, potassium, calcium, magnesium, chloride). Compared to photometric methods (e.g., flame photometry), they have the advantage that they permit continuous measurements as the build-up of potential at the electrode surface is reversible.

Despite the wide-spread use of electrochemical sensors based on ISEs and related devices incorporating field effect transistors, they are characterized by several disadvantages: They are comparatively large, which creates problems when they are used as catheters for in vivo applications. They require a reference electrode of approximately the same dimensions. The salt bridge necessary for such electrodes is particularly failure-prone. Finally, the measured result is easily affected by surface potentials of different origin.

SUMMARY OF THE INVENTION

It is an object of the present invention to present a sensor for determining electrolyte concentrations in aqueous solutions without incurring the above disadvantages and, in particular, to make a sensor suitable for in vivo applications.

According to the invention this is achieved by immobilizing a fluorescent indicator at the side of the ion-selective membrane facing towards the sample solution, whose fluorescence-intensity depends on the potential difference at the boundary surface between ion-selective membrane and sample solution. In the present invention the potential difference arising between the sample phase and a polymer membrane modified with an ion carrier, which is determined electrochemically with the ISE method, is measured by applying a suitable potential-sensitive fluorescent indicator to the boundary surface at which the potential difference arises, and by determining fluorescence intensity as a function of the electrolyte concentration. Thus the resulting difference in potential at the surface causes a change in the fluorescence intensity of the indicator which is proportional to the electrolyte concentration. In this way a sensor is created which is suitable for the measuring of blood electrolytes as well as other ions, and which does not require a reference electrode or a salt bridge.

Ion-selective membranes are ideally made of materials that are also used for producing carrier membranes for ISEs, such as PVC and similar materials. Other membrane-making materials include difunctional molecules, such as phosphatidyl fatty acids and others occurring in natural lipid membranes, for example. Preferred carriers should have a high specificity for the ion to be determined, but they should not allow other ions to diffuse into the membrane. Carriers with a high specificity are known for protons, potassium, sodium, calcium, lithium and chloride; together with the sensor described above they permit the development of a fluorescence-optical, continuous method for determining the most important blood electrolytes.

As potential-sensitive fluorescent indicators substances should be used whose dipole moment in the excited state differs from that in the normal state. In addition, these indicators should have several other properties: they should be stable, i.e., they should not be degraded by storage or exposure to light. If the fluorescent indicators are characterized by long-wave absorption and fluorescence peaks, this will permit photo-excitation by inexpensive light sources as well as the use of plastic optical fibers which are not transparent to ultraviolet radiation. Besides, a large Stokes' shift will ensure an efficient separation of fluorescent light and scattered excitation light as well as Raman light: Stokes' shift denoting the difference between the absorption peak of the indicator and its fluorescence peak.

Fluorescence-optical sensors of a non-potential-sensitive kind exist for use with a number of different ions, and are always based on the fact either that an indicator forms a reversible bond with the quantity to be measured, or that the fluorescence of the indicator is quenched, or—as in the instance of $CO_2$—that a shift of a preestablished acid-base equilibrium is observed by pH-measurement. So far fluorescent indicators for determining the most important blood electrolytes referred to above, have been lacking, however.

In a further development of the invention the potential-sensitive fluorescent indicator, together with the ion-selective membrane, is directly applied on a transparent carrier plate, preferably made of glass, through which the excitation light or fluorescent light is transmitted. In this way a stable carrier plate is obtained which is used as a vehicle for applying excitation light to the fluorescent indicator at the same time. The excitation light may also be propagated by total reflection inside a carrier element with plane-parallel surfaces until the refractive index of the adjoining indicator layer, which is higher than that of the environment, permits a passage through the boundary surface, and thus excitation of the indicator molecules.

In an enhanced variant of the invention the potential-sensitive fluorescent indicator, together with the ion-selective membrane, is in contact with the end of a light conductor, preferably an optical fiber, via the side of the membrane away from the fluorescent indicator. A measuring device of this kind may be designed for use as a fiber-optical catheter, for instance. In this case the sensor membrane consisting of an ion-selective membrane and a fluorescent indicator, is integrated into the tip of an optical fiber. Again the layer with the potential-sensitive fluorescent indicator is next to the sample. The excitation light is transmitted to the indicator by means of the optical fiber. The fluorescent light may either be carried by the same fiber or by the other strand of a two-strand optical fiber. Suitable light sources include tungsten and halogen lamps, gas discharge lamps, light-emitting diodes (LEDs), lasers, etc. Their choice will depend on the analytical problem posed and the nature of the indicator.

One of the major advantages of such optical sensors is that they may be kept very small. For instance, fiber-optical oxygen catheters have been described with a diameter of 0.2 mm. Besides, unlike electro-chemical sensors, the optical sensors do not require reference electrodes or salt bridges.

Preferably, application of the fluorescent indicators to the boundary surface between aqueous and polymer phase is performed by physical or chemical immobilization, either on a carrier substance or directly on the polymer phase. The advantage of immobilization is that the indicator cannot be washed out by the sample substance. Suitable immobilization techniques are the same as for immobilizing organic molecules, and have been thoroughly discussed in numerous publications. Special immobilization techniques for indicators are described in DE-OS 28 51 138.

DESCRIPTION OF THE DRAWINGS

Following is a more detailed discussion of further variants of the invention and their advantages, as illustrated by the accompanying drawings in which.

DETAILED DESCRIPTION OF THE PREFERRED EMBODIMENTS

Figure 1:
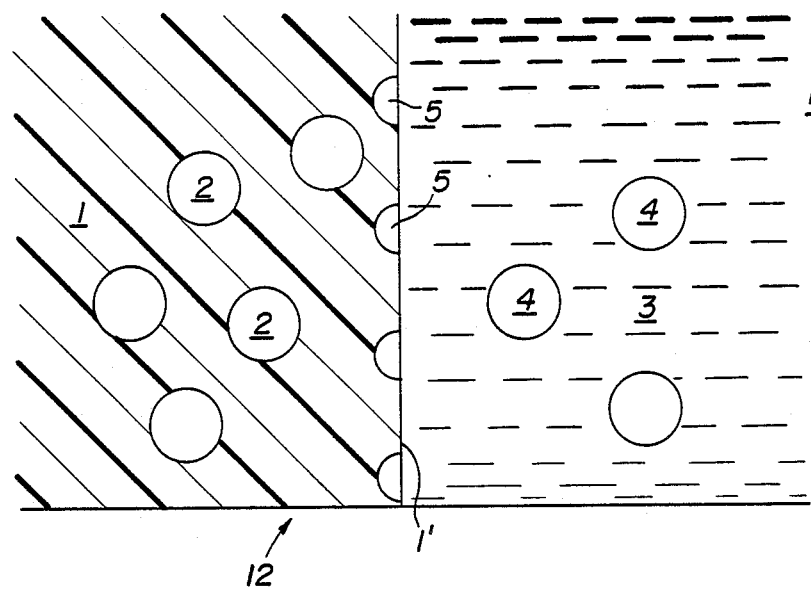
FIG. 1 is the functional diagram of a sensor as described by the invention.
Figure 2:
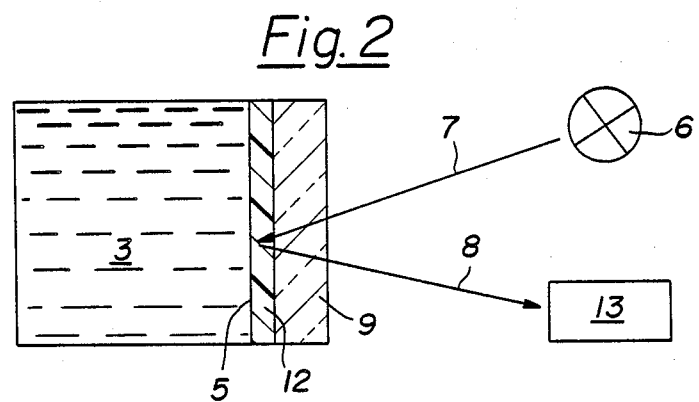
FIGS. 2 and 3 present possible measuring arrangements and positions of the sensor.

As shown in FIG. 1 an ion-selective membrane 1, for instance a polymer layer, contains the carrier molecules 2 and, at its surface, the fluorescent indicator 5 whose fluorescence is potential-sensitive. In front of the polymer layer there is the sample solution 3 containing the electrolyte 4 which is introduced partially into the polymer layer via the carrier molecules 2. The indicator molecules of the fluorescent indicator 5 are immobilized at the polymer layer either chemically or physically. The potential difference at the surface resulting from the ion transport leads to a change in the fluorescence intensity of the indicator which is then measured. The sensor membrane consisting of the ion-selective membrane 1 and the potential-sensitive fluorescent indicator 5 is denoted 12 in FIG. 1. FIG. 2 is a schematic drawing of a measuring arrangement (an Aminco SPF 500 spectrofluorimeter in this instance) in which the sensor membrane 12 is directly applied to a glass carrier plate 9. The excitation light 7 coming from a light source 6 strikes the sensor membrane 12 whose fluorescent indicator 5 is immobilized on the surface facing the sample solution 3. The fluorescence light 8 is transmitted to a detection/evaluation unit 13 in a conventional way.

Following is an example for the preparation of a potassium-sensitive sensor membrane.

Dissolve 2 mg valinomycin, 2 mg potassium-tetrakis-chlorophenyl borate, 30 mg PVC and 66 mg dioctyl phtalate in 10 ml tetrahydrofuran. Apply 0.2 ml of this solution to a glass slide (2.5×2.6 cm). Evaporate at room temperature. The glass slide will not only serve as a solid support during preparation of the membrane but may also be used later on as a membrane carrier in the optical sensor which is characterized by optical transparency and good physical properties. Before the solvent has completely evaporated approximately 5 mg of commercially available aminoethyl cellulose should be sprinkled on. After complete drying part of the aminoethyl cellulose will adhere to the PVC surface, the rest should be blown off.

Immobilization of the potential-sensitive indicator rhodamine B at the boundary surface is achieved by covalent bonding to the amine groups of the aminoethyl cellulose. For this purpose a solution of 2 mg EDC (1-ethyl-3-(3-dimethylaminopropyl)carbon diimide x HCl) and 5 mg rhodamine B in 5 ml water should be prepared. After dropping 0.5 ml of this solution onto the PVC membrane described above the preparation should be allowed to stand for 18 hours. The liquid remains should then be removed and the product rinsed with water for several times.

The pink-colored sensor membrane obtained in this manner will then be ready for use. In a measuring arrangement as shown in FIG. 2 it may serve for determining potassium concentrations.

Figure 3:
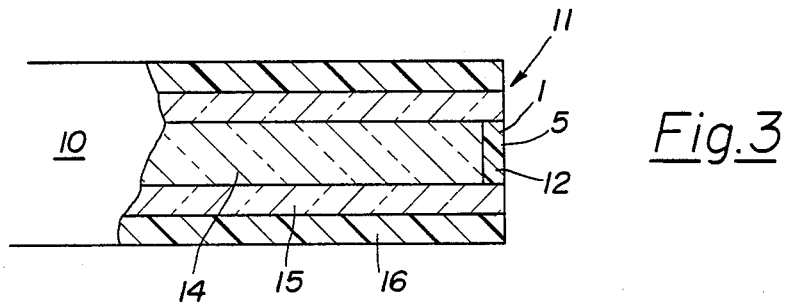

FIG. 3 shows a measuring arrangement configured as a fiber-optical catheter in which the sensor membrane 12 is applied to the end of an optical fiber 10 consisting of a core 14 which is surrounded by a coat 15. This in turn is surrounded by a protective sleeve 16. It will also be possible to use optical fibers without coating. The potential-sensitive fluorescent indicator 5 is on the side facing the sample solution 3. Both excitation light and fluorescence light are transmitted via the optical fiber.

In another variant a multi-core optical fiber configured as a catheter is used for supplying excitation light to a sensor membrane 12, or transmitting fluorescence light towards the detector. Finally, the potential sensitive sensor layer may be applied to the core of the optical fiber 14 instead of the coat 15, fluorescence being excited in this case through a so-called evanescent wave. The term evanescent wave denotes the part of the electromagnetic filled penetrating into the coating upon total reflection at the boundary surface, for instance at the boundary core/coating of an optical fiber. Its intensity in the coating will decrease exponentially, a mean penetration depth of a few nanometers being sufficient to excite an indicator in this area to fluoresce.

Figure 4:
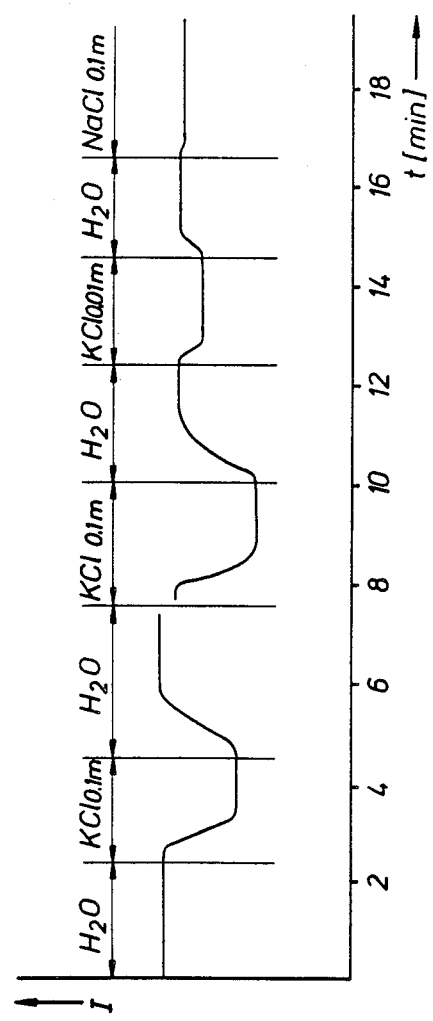
FIG. 4 presents a measuring signal obtained with an arrangement as in FIG. 2.

FIG. 4 shows the signal which is produced by a membrane manufactured as described above and is used in a measuring arrangement as shown in FIG. 2, when potassiumchloride solutions of different concentrations indicated by their molarity m flow past the membrane; the relative fluorescence intensity I is recorded against time t in minutes. It should be noted that the signal drop is almost exclusively due to potassium ions while sodium ions produce no appreciable effect.

A sensor membrane which is sensitive to sodium ions is obtained in the same way as in the example given above, with the exception that instead of valinomycin a sodium carrier is used, e.g., N,N'-bibenzyl-N,N'-diphenyl-1,2-phenylenedioxide-diacetamide. By suitable choice of the carrier membranes with a pronounced selectivity for the ion of interest may be produced.

Another example describe; the preparations of a potassium-sensitive sensor membrane with electrostatic immobilization.

The cation exchanger is prepared by sulphonation of a bead polymerizate: In a 250 ml three-neck bottle with a stirrer, a reflux condenser and a thermometer a mixture of 0.1 g silver nitrate and 75 ml concentrated sulphuric acid should be heated to 80° C., after which 10 mg of a copolymer consisting of 98% styrene and 2% divinyl benzene should be stirred in. Hold temperature at 100° C. for 3 hours and allow to cool off slowly afterwards. Stir the content of the bottle into 250 ml of a 50% sulphuric acid; after cooling dilute the mixture obtained in this way with distilled water. The beads which are of a gold-brown color, should be filtered off by suction, rinsed with water and dioxan, and dried in the desiccator. Valinomycin is incorporated into the ion exchanger by incubating 200 mg ion exchanger plus 2.8 mg valinomycin together with 1 ml tetrahydrofuran for 24 hours. After this period the tetrahydrofuran should be removed, and the plastic pellets should be left to dry in the desiccator over night.

For immobilization of rhodamine B at the ion exchanger toss the dry ion exchanger for 5 minutes in 4 ml of an aqueous solution containing 0.5 mg rhodamine B. Filter off product, rinse with water and allow to dry in the desiccator. Finally, dissolve 30 mg polyvinyl chloride and 66 mg dioctyl phtalate in 10 ml tetrahydrofuran. Drop 0.2 ml of this solution onto a 2.5×2.8 cm glass slide. The solvent will evaporate at room temperature. During evaporation the sulphonated copolymer with the immobilized rhodamine B will be deposited. After drying the sensor membranes may be used for potassium determination.

In a third example the preparation of a sodium-sensitive sensor membrane is described, involving immobilization of rhodamine B at a glass substrate.

For amine modification 30 ml toluene (absolute) should be mixed with 3 ml toluene (water-saturated). Add to this mixture 0.15 ml triethoxysilyl propylamine, 30 mg tosyl chloride and 100 mg CPG (controlled porous glass, 500 A). This reactive mix should be cooked at reflux for 2 hours. After cooling rinse CPG pellets with toluene and acetone. Allow to dry for 3 hours at 100° C.

At the CP glass substrate obtained in this manner rhodamine is immobilized by coupling with the use of EDC reagent. For this purpose 50 ml water containing 5 mg EDC and 11 mg rhodamine B should be added to the dry CPG pellets which should then be allowed to rest at room temperature for 6 hours. After this period another 5 mg of EDC should be added, and the same quantity again after 16 hours. Hold for 6 hours. Filter off product, rinse with water and acetone and dry for 3 hours at 100° C.

We claim:

1. A sensor for determining the concentration of an electrolyte in an aqueous sample solution, said sensor comprising an ion-selective membrane which contains valinomycin as an ion-carrier material and which has a first side that can be brought into contact with an electrolyte-containing aqueous sample solution, and a potential-sensitive fluorescent indicator immobilized at said first side of said ion-selective membrane, said fluorescent indicator, when excited, emitting fluorescence having an intensity which is dependent on a potential difference which arises at the boundary surface between said ion-selective membrane and said electrolyte-containing aqueous sample solution due to ion transport from said sample solution into said ion-selective membrane at said boundary surface by means of said ion-carrier material, said fluorescence intensity corresponding to the concentration of electrolyte in the electrolyte-containing aqueous sample solution.

2. A sensor according to claim 1, wherein said ionselective membrane includes a second side, and wherein said sensor includes a transparent carrier plate supporting said second side of said ion-selective membrane.

3. A sensor according to claim 2, wherein said transparent plate is composed of glass.

4. A sensor according to claim 1, wherein said ionselective membrane includes a second side which is opposite to said first side, and including a light conductor having an end in contact with said second side of said ion-selective membrane.

5. A sensor according to claim 4, wherein said light conductor is an optical fiber.

6. A sensor according to claim 4, wherein said potential-sensitive fluorescent indicator is rhodamine B.

7. A sensor according to claim 4, wherein said ion-selective membrane comprises a polymer membrane having a first side that can be brought into contact with an electrolyte-containing aqueous sample solution, and wherein said ion-carrier material is located at said first side of said polymer membrane.

8. A sensor for determining the concentration of an electrolyte in an aqueous sample solution, said sensor comprising an ion-selective membrane which contains N,N'-bibenzyl-N,N'-diphenyl-1, 2-phenylenedioxide-diacetamide as an ion-carrier material and which has a first side that can be brought into contact with an electrolyte-containing aqueous sample solution, and a potential-sensitive fluorescent indicator immobilized at said first side of said ion-selective membrane, said fluorescent indicator, when excited, emitting fluorescence having an intensity which is dependent on a potential difference which arises at the boundary surface between said ion-selective membrane and said electrolyte-containing aqueous sample solution due to ion transport from said sample solution into said ion-selective membrane at said boundary surface by means of said ion-carrier material, said fluorescence intensity corresponding to the concentration of electrolyte in the electrolyte-containing aqueous sample solution.

9. A sensor according to claim 8, wherein said ion-selective membrane includes a second side, and wherein said sensor includes a transparent carrier plate supporting said second side of said ion-selective membrane.

10. A sensor according to claim 9, wherein said transparent plate is composed of glass.

11. A sensor according to claim 8, wherein said ion-selective membrane includes a second side which is opposite to said first side, and including a light conductor having an end in contact with said second side of said ion-selective membrane.

12. A sensor according to claim 11, wherein said light conductor is an optical fiber.

13. A sensor according to claim 11, wherein said potential-sensitive fluorescent indicator is rhodamine B.

14. A sensor according to claim 11, wherein said ion-selective membrane comprises a polymer membrane having a first side that can be brought into contact with an electrolyte-containing aqueous sample solution, and an ion-carrier material at said first side of said polymer membrane.

* * * * *